United States Patent [19]

Chen

[11] Patent Number: 5,567,441
[45] Date of Patent: Oct. 22, 1996

[54] DILTIAZEM CONTROLLED RELEASE FORMULATION

[75] Inventor: Chih-Ming Chen, Cooper City, Fla.

[73] Assignee: Andrx Pharmaceuticals Inc., Ft. Lauderdale, Fla.

[21] Appl. No.: 409,449

[22] Filed: Mar. 24, 1995

[51] Int. Cl.⁶ .............................. A61K 9/58; A61K 9/60; A61K 9/62
[52] U.S. Cl. .................... 424/494; 424/458; 424/461; 424/462; 424/468; 424/496; 424/497; 514/963
[58] Field of Search ...................... 424/490, 494, 424/5, 497, 458, 461, 462, 468, 496

[56] References Cited

U.S. PATENT DOCUMENTS

| | | | |
|---|---|---|---|
| 4,721,619 | 1/1988 | Panoz et al. | 424/459 |
| 4,839,177 | 6/1989 | Colombo et al. | 424/482 |
| 4,891,230 | 1/1990 | Geoghegan et al. | 424/461 |
| 4,894,240 | 1/1990 | Geoghegan et al. | 424/497 |
| 4,917,899 | 4/1990 | Geoghegan et al. | 424/461 |
| 5,002,776 | 3/1991 | Geoghegan et al. | 424/497 |
| 5,229,135 | 7/1993 | Philippon et al. | 424/494 |
| 5,260,068 | 11/1993 | Chen | 424/451 |
| 5,260,069 | 11/1993 | Chen | 424/451 |
| 5,286,497 | 2/1994 | Hendrickson et al. | 424/490 |
| 5,288,505 | 2/1994 | Deboeck et al. | 424/497 |
| 5,336,504 | 8/1994 | Geoghegan et al. | 424/462 |
| 5,364,620 | 11/1994 | Geoghegan et al. | 424/497 |

Primary Examiner—James M. Spear
Attorney, Agent, or Firm—Hedman Gibson & Costigan

[57] ABSTRACT

A once-a-day controlled release diltiazem formulation is described which includes:

(a) from 20 to 50% by weight of enteric polymeric membrane coated pellets comprising a polymer membrane coated core which comprises a biologically inert core which is coated with a first layer which consists essentially of diltiazem and a polymeric binder; and a second layer which comprises a membrane comprising a pH dependent polymeric material; and (b) from 50% to 80% by weight of delayed pulse polymeric membrane coated pellets comprising a polymeric membrane coated core which comprises a biologically inert core which is coated with a first layer which consists essentially of diltiazem and a polymeric binder and a second layer which comprises a polymeric membrane which will substantially maintain its integrity in the varying pH conditions of the gastrointestinal tract but is permeable to diltiazem; and (c) a unit dose containment system.

5 Claims, 5 Drawing Sheets

DILTIAZEM CONTROLLED RELEASE FORMULATION

BACKGROUND OF THE INVENTION

The present invention relates to controlled release unit dose formulations of diltiazem hydrochloride (diltiazem). Diltiazem is sold commercially in extended release pharmaceutical dosage forms in order to maintain a therapeutic serum level of diltiazem and to minimize the effects of missed doses of drugs caused by a lack of patient compliance. The minimum therapeutic plasma diltiazem concentrations are in the range of 50 to 200 ng/ml.

In the prior art extended release formulations of diltiazem tablets have been marketed which provide 24 hour therapeutic blood levels of diltiazem with once a day administration of a single dosage unit. Cardizem® CD is described as a once-a-day extended release capsule containing diltiazem and fumaric acid. In the file history of U.S. Pat. No. 5,286,497, representations were made that the formulation disclosed in that patent is the formulation for Caridizem® CD. The formulation for Cardizem® CD is identified in the file history of U.S. Pat. No. 5,286,497 as having a "stair-step release profile" which has a rapid release bead and an extended release bead.

The other commercially available diltiazem once-a-day formulation is sold under the Dilacor XR® trademark. This formulation is described as being based on the Geomatrix" controlled release system which is described in U.S. Pat. No. 4,839,177.

In U.S. Pat. No. 5,229,135, a once-a-day formulation is described that is based on a single pellet which is prepared with an active core which is coated with diltiazem and an inner and outer membrane.

Other diltiazem formulations are disclosed in U.S. Pat. No. 4,721,619; U.S. Pat. No. 4,894,240; U.S. Pat. No. 5,002,776; U.S. Pat. No. 5,364,620; U.S. Pat. No. 4,891,230; U.S. Pat. No. 4,917,899; U.S. Pat. No. 5,288,505; and U.S. Pat. No. 5,336,504.

The present invention provides a novel diltiazem once-a-day formulation two-pellet based capsule formulation which does not have a "stair-step release profile" and does not require the presence of fumaric acid or any other organic acid.

SUMMARY OF THE INVENTION

The present invention is directed to a once-a-day controlled release diltiazem formulation which comprises:

(a) from 20 to 50% by weight of enteric polymeric membrane coated pellets comprising a polymer membrane coated core which comprises a biologically inert core which is coated with a first layer which consists essentially of diltiazem and a polymeric binder; and a second layer which comprises a membrane comprising a polymeric enteric coating material; and (b) from 50% to 80% by weight of delayed pulse polymeric membrane coated pellets comprising a polymeric membrane coated core which comprises a biologically inert core which is coated with a combined first layer which consists essentially of diltiazem and a polymeric binder polymer and a second layer which comprises a polymeric membrane which will substantially maintain its integrity in the varying pH conditions of the gastrointestinal tract but is permeable to diltiazem; and (c) a unit dose containment system.

The present invention provides a dosage form which exhibits in 0.1N HCl, a release rate profile which is initially a relatively slow, zero order release rate that continues for up to about 12–14 hours. Thereafter, there is a sharp increase in the rate of release which can be characterized as a delayed pulse. It is surprising and unexpected that the combined zero order-delayed pulse in vitro release characteristics of the dosage form of the present invention provides substantially the same in vivo plasma levels of diltiazem which is provided by a commercial formulation which exhibits in vitro a stair-step type of release profile.

It is an object of the invention to provide a a once-a-day diltiazem dosage system.

It is also an object of the present invention to provide a once-a-day diltiazem dosage system which is free of any organic acid component.

It is also an object of this invention to provide a once-a-day diltiazem dosage system which avoids the initial high plasma level of diltiazem which is inherent in a once-a-day stair step diltiazem dosage system.

It is also an object of this invention to provide a once a day diltiazem dosage system which has a zero order release dissolution profile of diltiazem initially which is followed by a delayed pulse release of diltiazem.

It is also an object of this invention to provide an organic acid free, once-a-day diltiazem dosage system which is therapeutically or biologically equivalent to a once-a-day stair step diltiazem dosage system which contains an organic acid.

It is also an object of this invention to provide a once a day diltiazem dosage system which provides a diltiazem serum concentration of from 50 to 200 ng/ml.

These and other objects of the invention will become apparent from the appended specification.

DETAILED DESCRIPTION OF THE INVENTION

Figure 1:
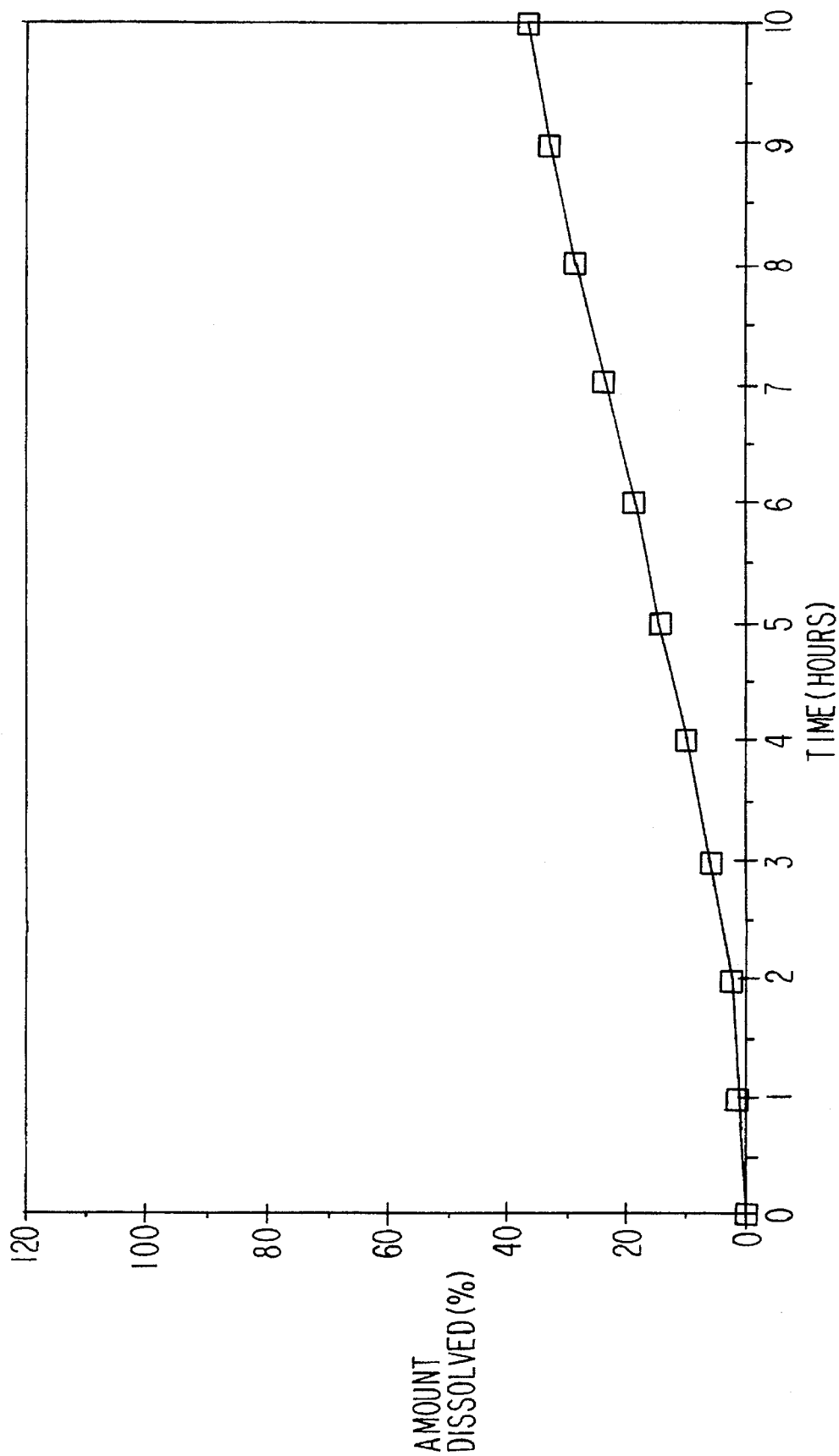
FIG. 1 is a graph which shows the slow, zero order, in vitro dissolution rate of diltiazem from enteric polymer membrane coated core pellets prepared according to the present invention in simulated gastric fluid using a USP Type II apparatus at 37° 100 rpm.

The once-a-day diltiazem controlled release formulation of the invention provides an alternative to the prior art formulations which require the presence of an organic acid to achieve a once-a-day effect.

Both the enteric polymer membrane coated pellet and the delayed pulse polymer membrane coated pellet are based on an active core which contains the diltiazem hydrochloride. The core is made by coating a biologically inactive core component such as non-pareil sugar particles, sugar spheres, starch granules, clay particles or other material on which may be deposited a coating of diltiazem hydrochloride in combination with a polymeric binder which comprises from 5 to 10 wt. % (based on the combined weight of the binder and the diltiazem) and of a polymeric material such as ethylcellulose, polyvinylpyrrolidone, hydroxypropyl methylcellulose and hydroxypropylcellulose. The binder is applied using conventional solvents which are removed from the product during processing.

The active core component is provided with an enteric coating which is a polymeric enteric coating material. The enteric coatings are "pH dependent" which describes the well known effect of an enteric coating which prevents release of the dosage form in the low pH conditions of the stomach but permits release in the higher pH conditions of the small intestine. The enteric coating will comprise from 4 to 10% preferably from 5 to 8% by weight based on the combined weight of the active core component and the total weight of the coating. The enteric coating polymer may be selected from the group consisting of shellac, methacrylic acid copolymers, (Eudragit S or L) cellulose acetate phthalate, hydroxypropylmethylcellulose phthalate, hydroxypropylmethylcellulose acetate succinate, cellulose acetate trimellitate and polyvinyl acetate phthalate. Methacrylic acid copolymer, Type B USP/NFXXII which dissolves at a pH above about 7.0 is preferred. The thickness of the coating is selected to provide the desired release rate depending on the thickness of the coating and the particular coating.

A commercially available copolymer is Eudragit S100 which is based on methacrylic acid and methyl methacrylate and has a weight average molecular weight of about 150,000. Other auxiliary coating aids such as a minor amount (1–5 wt. % based on the active core component and the total weight of the final coating) of a plasticizer such as acetyltributyl citrate, triacetin, acetylated monoglyceride, rape oil, olive oil, sesame oil, acetyltriethylcitrate, glycerin, sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, polyethyleneglycol (molecular weight of from 380 to 420), propylene glycol and mixtures thereof in combination with an antisticking agent which may be a silicate such as talc. The antisticking agent may be added in an amount which is equivalent to 0.3 to 1.0:1.0 by weight of the methacrylic acid copolymer. These components may be added to the methacrylic acid copolymer in combination with appropriate solvents.

The delayed pulse polymeric coated pellet contains an active core which is coated with a polymeric material which will substantially maintain its integrity in the varying pH conditions of the gastrointestinal tract but is permeable to diltiazem. The delayed pulse polymeric pellet is designed to release diltiazem in vitro about 10 to 12 hours after the dosage form of the invention is placed in 0.1N HCl. The rate of release for the delayed pulse pellet is sharply increased, i.e. about 3 to 5 times, as compared to the in vitro rate of release of the enteric coated diltiazem pellets of the invention. The delayed pulse pellet is made by coating the active core component with 15 to 22 wt. % and preferably from 17 to 19 wt. % (based on the combined weight of the active core and the total weight of the final coating) of a polymer such as ethyl cellulose, cellulose acetate, cellulose acetate butyrate, or an acrylic copolymer which when used in a sufficient amount will cause the delayed pulse pellet to release diltiazem 10 to 12 hours after the ingestion of the dosage form of the invention. Materials such as Eudragit RS 30D; RS 100; NE 30D; RL 30D or RL 100 may be used to prepare the delayed pulse pellet. A preferred material is an acrylate copolymer which has a permeability which is independent of pH. Such a preferred acrylate copolymer is commercially available as Eudragit RS30D which is available as a 30 wt. % aqueous dispersion of copolymers of acrylic and methacrylic acid esters, having a number average molecular weight of 150,000 with a low content of quaternary ammonium groups. Other auxiliary coating aids such as a minor amount (3–7 wt. % based on the active core component and the total weight of the final coating) of a plasticizer such as acetyltributyl citrate, triacetin, acetylated monoglyceride, rape oil, olive oil, sesame oil, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, polyethyleneglycol (molecular weight of from 380 to 420), propylene glycol and mixtures thereof in combination with an antisticking agent which may be a silicate such as talc in an amount which is equivalent to 0.3 to 0.75:1 by weight of the acrylate copolymer, may be added to the acrylate copolymer in combination with appropriate solvents.

The controlled release diltiazem formulation of the invention will preferably have a dissolution release rate in 0.1N HCl in a USP XXII Type II apparatus at 37° C. and 100 rpm which substantially corresponds to the following:

a) from 0 to 15 wt. % and preferably form 5 to 15 wt. % of total diltiazem is released after 6 hours;

b) from 10 to 30 wt. % and preferably from 15 to 25 wt. % of total diltiazem is released after 12 hours;

c) from 25 to 65 wt. % and preferably from 45 to 60 wt. % of total diltiazem is released after 18 hours;

d) not less than 70wt% and preferably not less than 80 wt. % of total diltiazem is released after 24 hours.

The enteric polymer pellets of the invention and the delayed pulse polymer membrane coated pellets may be placed in soft or hard gelatin capsules or in other dosage forms such as tablets which contain a cushioning agent to prevent damage to the pellets or the polyethylene glycol based dosage formulation which is disclosed in copending application Ser. No. 08/205,005, filed Mar. 2, 1994, U.S. Pat. No. 5,458,888 which is incorporated by reference.

Generally the dosage form will contain from about 20 to 50 wt. % and preferably about 40 wt. % of the enteric polymer membrane coated pellets and from about 50 to 80 wt. % and preferably about 60 wt. % of the delayed pulse polymer coated pellets.

DESCRIPTION OF THE PREFERRED EMBODIMENTS

EXAMPLE

A diltiazem hydrochloride active pellet (A) having the following formulation was prepared:

| | | |
|---|---|---|
| diltiazem hydrochloride, USP | 70.0 wt % | 16.8 kg |
| sugar spheres | 23.65 wt % | 5.676 kg |
| ethylcellulose, NF (Ethocel 10 cps) | 5.85 wt % | 1.404 kg |
| polysorbate 80 NF | 0.5 wt % | 0.12 kg |
| isopropyl alcohol, USP* | * | 31.42 kg |
| | 100.0 | 24.00 kg |

*evaporated during processing

The ethylcellulose is dissolved in the isopropyl alcohol in a 25 gallon stainless steel tank. The diltiazem hydrochloride is added to the ethylcellulose solution with continued agitation for 10 minutes with the homogenizer under conditions that avoid the introduction of air which will cause foaming. The polysorbate 80 is then added and stirring is continued for 2 minutes.

The diltiazem pellets (A) are then coated with the enteric polymer to form enteric polymer membrane coated diltiazem (B) pellets as follows:

| | | |
|---|---|---|
| diltiazem hydrochloride pellets (A) | 90.0 wt % | 3.60 kg |
| methacrylic acid copolymer (Eudragit S100) | 6.75 wt % | 0.27 kg |
| acetyltributyl citrate | 1.00 wt % | 0.04 kg |
| talc, USP | 2.25 wt % | 0.09 kg |
| isopropyl alcohol, USP | | 1.25 kg |
| acetone, NF | | 1.25 kg |
| | 100.0 | 4.00 |

The diltiazem hydrochloride pellets (A) are spray coated in a fluidized bed coater (GPCG5; nozzle 1.0 mm; and plate D) using a mixture which is prepared by combining the acetone and the isopropyl alcohol in a 4L beaker and adding the methacrylic acid copolymer (Eudragit S100) with mechanical stirring. The acetyltributyl citrate is then added with stirring until it dissolves. The talc is added and stirring is continued until all lumps are dispersed. The pellets larger than USS mesh #14 and smaller than USS mesh #25 are rejected.

The diltiazem hydrochloride pellets (A) are coated as follows to prepare the delayed pulse membrane coated extended release diltiazem hydrochloride pellets (C):

| | | |
|---|---|---|
| diltiazem hydrochloride pellets (A) | 69.4 wt % | 2.776 kg |
| acrylate copolymer (Eudragit RS30D) (30 wt % aqueous dispersion) | 18.0 wt % | 0.72 kg |
| talc | 9.0 wt % | 0.36 kg |
| acetyltributylcitrate (ATBC) | 3.6 wt % | 0.144 g |
| purified water, USP | | 5.35 kg |

The diltiazem hydrochloride pellets (A) are spray coated in a fluidized bed coater (GPCG 5; nozzle 1.0 mm; and plate D) using a mixture which is prepared by combining the talc and the ATBC in purified water in a 4L beaker and adding the acrylate copolymer (Eudragit RS 30D) and with mechanical stirring. The pellets are oven dried with 2 wt. % talc at 60° C. Any pellets larger than USS mesh #14 and smaller than USS mesh #25 are rejected.

Figure 2:
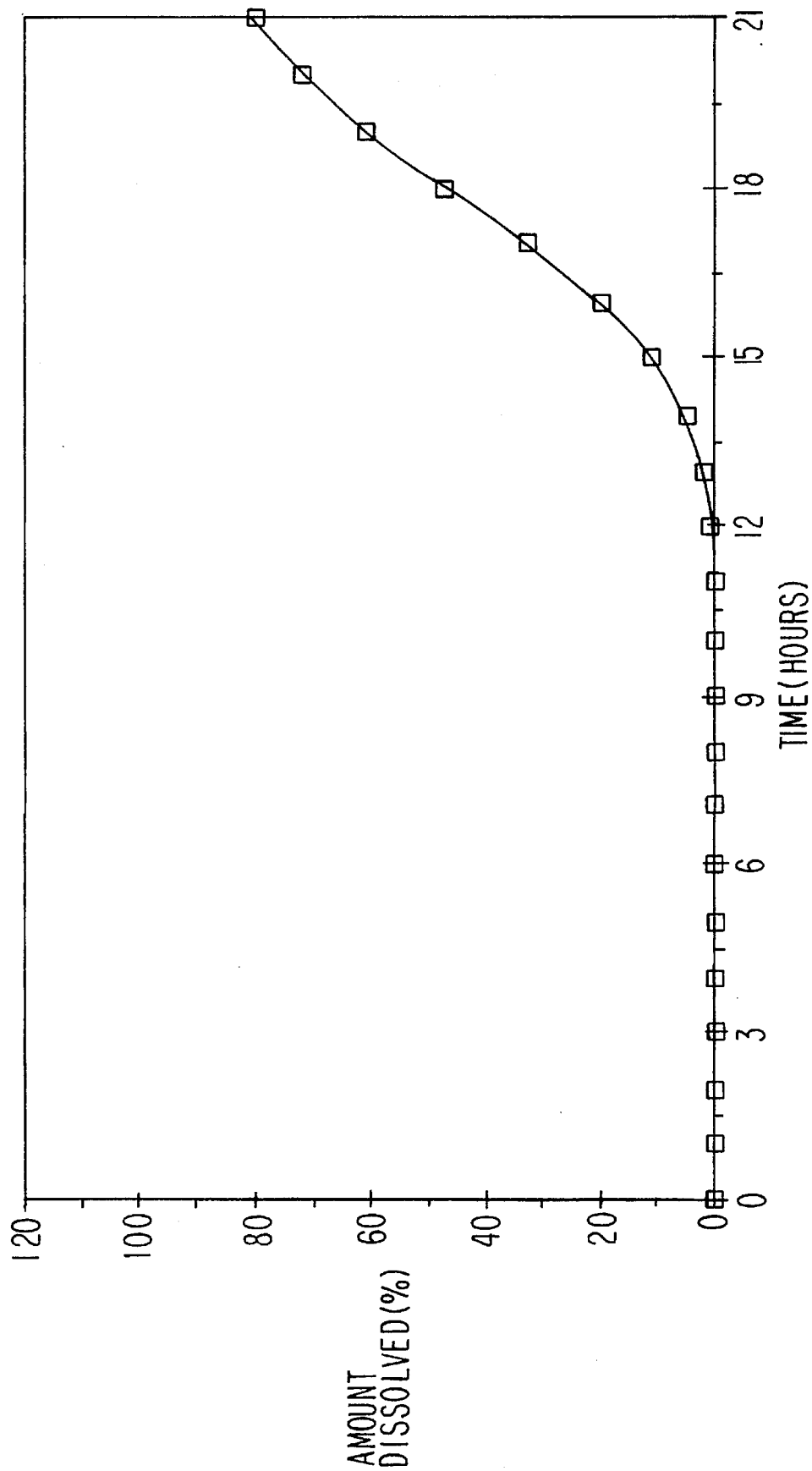
FIG. 2 is a graph which shows the in vitro dissolution rate of diltiazem delayed pulse membrane coated core pellets prepared according to the present invention in 0.1N HCl using a USP Type II apparatus at 37° 100 rpm.
Figure 3:
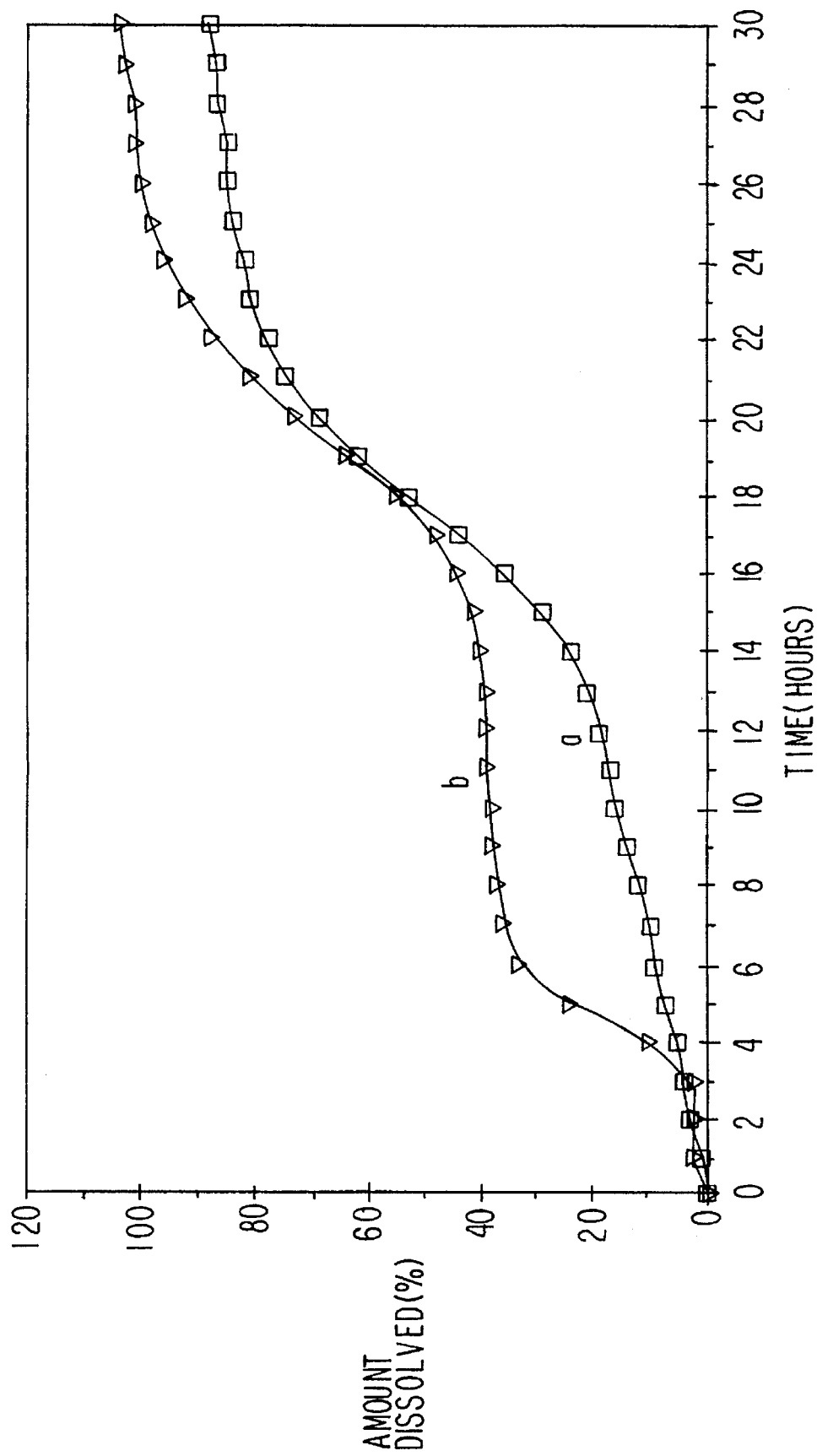
FIG. 3 includes curve (a) which shows the in vitro dissolution rate of a diltiazem formulation according the the Example which is a 60:40, by weight, mixture of the enteric coated pellets whose dissolution rate is shown in FIG. 1 and the delayed pulse coated pellets whose dissolution rate is shown in FIG. 2. The curve (b) was derived from the commercial product Cardizem® CD. Both curves were derived from testing in 0.1N HCl using a USP Type II apparatus at 37° 100 rpm.
Figure 4:
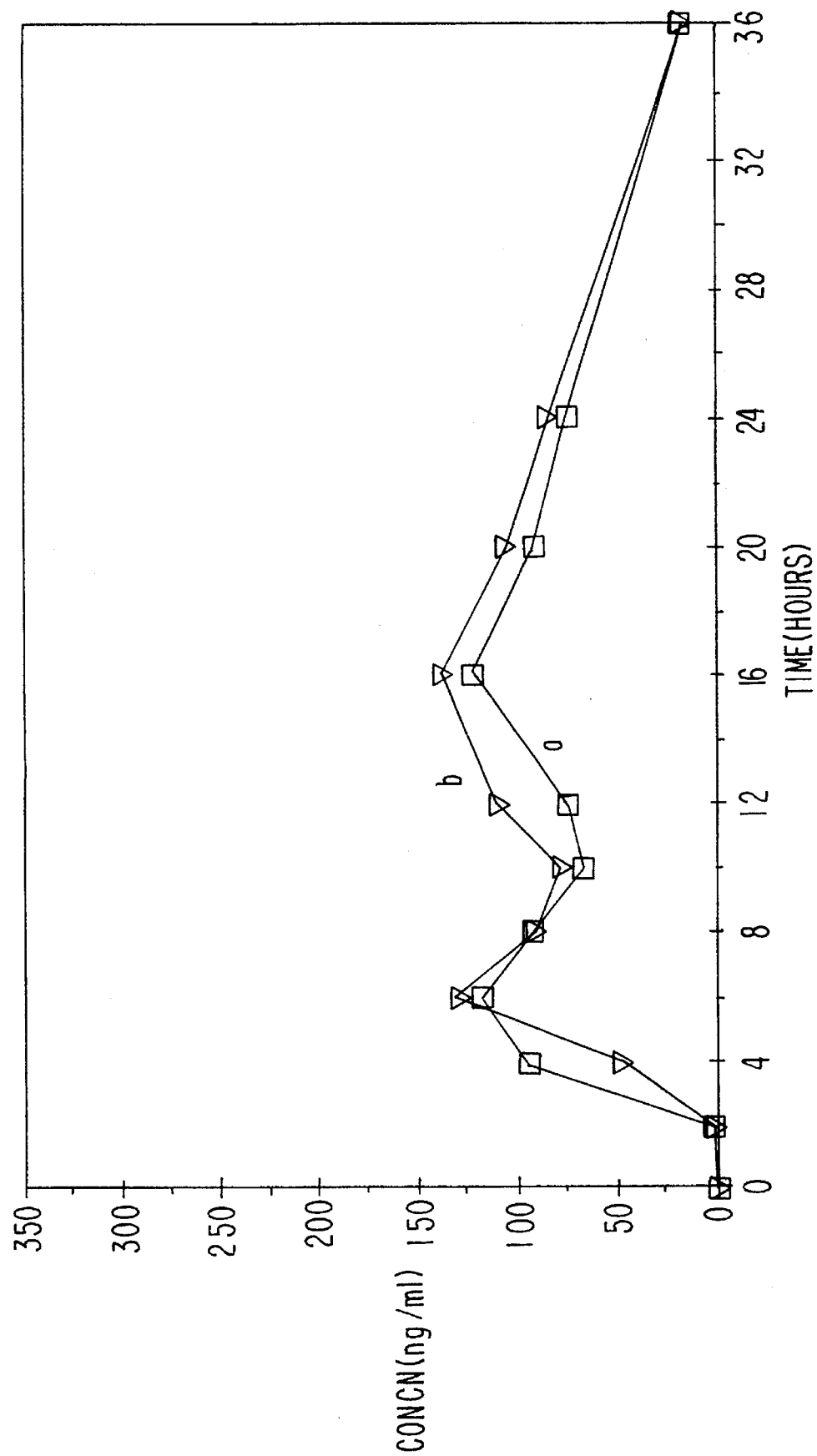
FIG. 4 includes curve (a) which shows the mean in vivo plasma levels obtained by the administration of the formulation which was tested in FIG. 3, in five healthy human volunteers who ingested the formulation without food and curve (b) which shows the mean plasma levels obtained from the commercial product Cardizem® CD (300 mg) in five healthly human subjects who ingested the formulation without food in a two way crossover study.

A blend of 40 wt. % of the enteric coated pellets (B) containing 120 mg of diltiazem HCl and 60 wt. % of the delayed pulse polymer membrane coated extended release pellets (C) containing 180 mg of diltiazem HCl was placed in a capsule (Capsule No. 00) and tested for percent dissolution/time in 900 ml of 0.1N HCl in a USP XXII type II apparatus at 100 rpm at 37° C. The results are shown in FIG. 3. Separate determinations of the dissolution percent/time of the enteric polymer membrane coated enteric pellets (B) and the delayed pulse extended release pellets (C) alone were carried out under identical conditions and the results are reported in FIG. 1 and FIG. 2. The data set forth on FIG. 4 shows the mean plasma levels in vivo for five patients who were given the formulation of the invention when fasting. The reference is Cardizem CD®. The test data shows that the formulation of the invention provides a plasma level of between 50 and 200 ng/ml for a 24 hour period.

Figure 5:
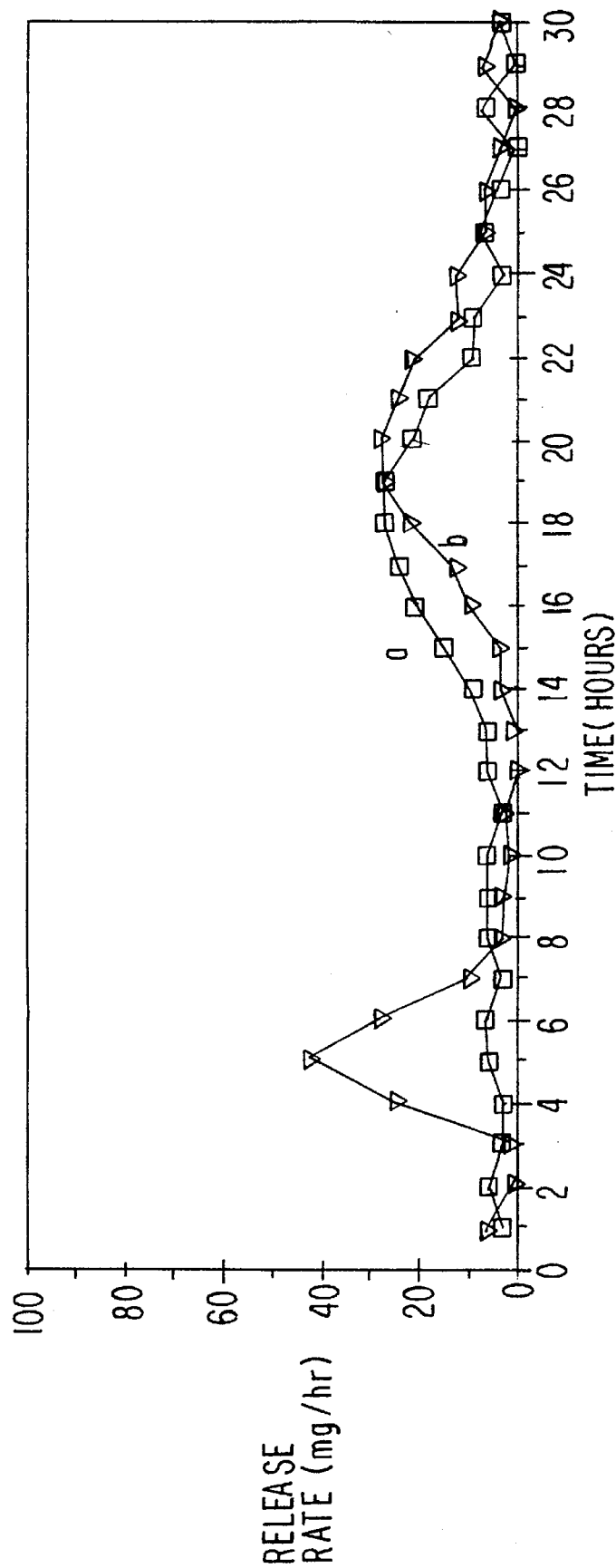
FIG. 5 includes curve (a) of the in vitro release-rate profile of a dosage formulation of the invention which is compared to curve (b) which shows the release-rate profile of Cardizem® CD. The data for both curve (a) and (b) were derived from the data of FIG. 3.

FIG. 5 is a curve of the in vitro release-rate profile of a dosage formulation of the invention that is derived from FIG. 3 which is compared to the release-rate profile of Cardizem® CD under the same conditions. This data shows that the formulation of the invention has an initial zero order release profile and a delayed pulse release while Cardizem® CD has an in vitro release-rate profile that has two distinct pulses.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

I claim:

1. A once-a-day controlled release diltiazem formulation which comprises:

(a) from 20 to 50% by weight of enteric polymer membrane coated pellets comprising a polymer membrane coated core which comprises a biologically inert core which is coated with a first layer which consists essentially of diltiazem and a polymer binder; and a second layer which comprises a membrane comprising polymer enteric coating material selected from the group consisting off shellac, methacrylic acid copolymers and cellulose acetate phthalate; and (b) from 50% to 80% by weight of delayed pulse polymer membrane coated pellets comprising a polymer membrane coated core which comprises a biologically inert core which is coated with a first layer which consists essentially of diltiazem and a polymer binder and a second layer which comprises a polymer membrane which will maintain its integrity in the varying pH conditions of the gastrointestinal tract but is permeable to diltiazem; and (c) a unit dose containment system.

2. A once-a-day controlled release diltiazem formulation as defined in claim 1 wherein the enteric coating polymer material and the second layer on the delayed pulse pellets both contain a plasticizer.

3. A once-a-day controlled release diltiazem formulation as defined in claim 1 wherein the membrane on the enteric coating polymer material is a methacrylic acid copolymer.

4. A once-a-day controlled release diltiazem formulation as defined in claim 1 wherein the second layer on the delayed pulse polymer membrane coated pellets is a copolymer of acrylic and methacrylic acid esters.

5. A once-a-day controlled release diltiazem formulation which comprises:

(a) from 20 to 50% by weight of enteric polymeric membrane coated pellets comprising a polymer membrane coated core which comprises a biologically inert core which is coated with a first layer which consists essentially of diltiazem, a polymer binder and polysorbate 80; and a second layer which comprises a membrane comprising polymer enteric coating material which comprises polymethacrylic acid and ethylacrylate; and (b) from 50% to 80% by weight of delayed pulse polymer membrane coated pellets comprising a polymeric membrane coated core which comprises a biologically inert core which is coated with a first layer which consists essentially of diltiazem and a polymer binder and a second layer which comprises a polymer membrane which will maintain its integrity in the varying pH conditions of the gastrointestinal tract but is permeable to diltiazem; and (c) a unit dose containment system.

* * * * *